United States Patent
Viker et al.

(10) Patent No.: US 9,943,392 B2
(45) Date of Patent: Apr. 17, 2018

(54) IMPLANTS, TOOLS, AND METHODS FOR TREATMENT OF PELVIC CONDITIONS

(75) Inventors: Thomas O. Viker, Arden Hills, MN (US); James A. Alexander, Excelsior, MN (US); Micah D. Thorson, North Branch, MN (US); Chaouki A. Khamis, Edina, MN (US); Justin H. Huelman, Lino Lakes, MN (US); William S. Tremulis, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 458 days.

(21) Appl. No.: 14/115,245

(22) PCT Filed: May 4, 2012
(Under 37 CFR 1.47)

(86) PCT No.: PCT/US2012/036575
§ 371 (c)(1),
(2), (4) Date: Mar. 27, 2014

(87) PCT Pub. No.: WO2012/151516
PCT Pub. Date: Nov. 8, 2012

(65) Prior Publication Data
US 2014/0343579 A1 Nov. 20, 2014

Related U.S. Application Data

(60) Provisional application No. 61/482,430, filed on May 4, 2011, provisional application No. 61/496,127, filed on Jun. 13, 2011.

(51) Int. Cl.
*A61B 17/42* (2006.01)
*A61B 17/46* (2006.01)
(Continued)

(52) U.S. Cl.
CPC ........ *A61F 2/0063* (2013.01); *A61B 17/3209* (2013.01); *A61B 17/320016* (2013.01);
(Continued)

(58) Field of Classification Search
CPC ........ A61B 17/0467; A61B 17/320016; A61B 17/3209; A61B 17/42; A61B 2017/00805;
(Continued)

(56) References Cited

U.S. PATENT DOCUMENTS

| 4,848,341 A | 7/1989 | Ahmad et al. |
|---|---|---|
| 5,824,008 A | 10/1998 | Bolduc et al. |

(Continued)

FOREIGN PATENT DOCUMENTS

| WO | WO 2007/016083 | 2/2007 |
|---|---|---|
| WO | WO 2007/016141 | 2/2007 |

(Continued)

OTHER PUBLICATIONS

Laparoscopic Sacral Colpopexy. Procedure [online]. Mikos and Moore. Dec. 18, 2010 (Dec. 18, 2010). [retrieved on Aug. 12, 2012]. Retrieved from the Internet<URL: web.archive.org/web/20101218101256/http://mikiosandmoore.com/lap_proc8a.php>. pp. 2-3.

(Continued)

*Primary Examiner* — Melanie Tyson
(74) *Attorney, Agent, or Firm* — Brake Hughes Bellermann LLP

(57) ABSTRACT

An adjusting and cutting tool including a distal end engageable with an elongate portion of an implantable article to facilitate manipulation of the elongate portion relative to a support portion of the implantable article and to facilitate cutting of the elongate portion. Also included is method of treating vaginal prolapse, the method including the steps of providing a multi-piece implantable article having at least (Continued)

one extension portion piece and a support portion piece, placing the support portion piece in contact with vaginal tissue, placing at least one extension portion piece in contact with tissue of a component of sacral anatomy, adjusting a position of the at least one extension portion piece relative to the support portion piece using a adjusting and cutting tool, and cutting the at least one extension portion with the adjusting and cutting tool.

14 Claims, 11 Drawing Sheets

(51) Int. Cl.
| | |
|---|---|
| A61D 1/10 | (2006.01) |
| A61F 2/00 | (2006.01) |
| A61B 17/32 | (2006.01) |
| A61B 17/3209 | (2006.01) |
| A61B 17/04 | (2006.01) |
| A61B 17/00 | (2006.01) |

(52) U.S. Cl.
CPC ........ *A61F 2/0045* (2013.01); *A61B 17/0467* (2013.01); *A61B 17/42* (2013.01); *A61B 2017/00805* (2013.01); *A61B 2017/32004* (2013.01); *A61F 2002/0072* (2013.01); *A61F 2250/0007* (2013.01); *A61F 2250/0064* (2013.01)

(58) Field of Classification Search
CPC ........... A61B 2002/0072; A61F 2/0063; A61F 2/0031; A61F 2/0045
See application file for complete search history.

(56) References Cited

U.S. PATENT DOCUMENTS

| | | | |
|---|---|---|---|
| 5,827,310 A | 10/1998 | Marin et al. | |
| 5,830,221 A | 11/1998 | Stein et al. | |
| 5,830,231 A | 11/1998 | Geiges, Jr. | |
| 5,860,993 A * | 1/1999 | Thompson | A61B 17/0467 30/151 |
| 6,077,277 A | 6/2000 | Mollenauer | |
| 6,254,620 B1 | 7/2001 | Koh et al. | |
| 6,328,749 B1 | 12/2001 | Kalmann et al. | |
| 6,612,977 B2 | 9/2003 | Staskin et al. | |
| 6,648,921 B2 | 11/2003 | Anderson et al. | |
| 6,691,711 B2 | 2/2004 | Raz et al. | |
| 7,025,063 B2 | 4/2006 | Snitkin et al. | |
| 7,070,556 B2 | 7/2006 | Anderson et al. | |
| 7,189,251 B2 | 3/2007 | Kay | |
| 7,303,525 B2 | 12/2007 | Watschke et al. | |
| 7,347,812 B2 | 3/2008 | Mellier | |
| 7,351,197 B2 | 4/2008 | Montpetit et al. | |
| 7,407,480 B2 | 8/2008 | Staskin et al. | |
| 7,422,557 B2 | 9/2008 | Arnal et al. | |
| 7,500,945 B2 | 3/2009 | Cox et al. | |
| 7,722,528 B2 | 5/2010 | Arnal et al. | |
| 7,740,576 B2 | 6/2010 | Hodroff et al. | |
| 7,901,346 B2 | 3/2011 | Kovac et al. | |
| 7,905,825 B2 | 3/2011 | Arnal et al. | |
| 7,914,437 B2 | 3/2011 | Gozzi et al. | |
| 2002/0028980 A1 | 3/2002 | Thierfelder et al. | |
| 2002/0087178 A1* | 7/2002 | Nobles | A61B 17/0467 606/167 |
| 2002/0147382 A1 | 10/2002 | Neisz et al. | |
| 2002/0151762 A1 | 10/2002 | Rocheleau et al. | |
| 2005/0277985 A1* | 12/2005 | Wert | A61B 17/06166 606/228 |
| 2006/0069301 A1 | 3/2006 | Neisz et al. | |
| 2006/0178682 A1* | 8/2006 | Boehlke | A61B 17/0057 606/148 |
| 2006/0195007 A1 | 8/2006 | Anderson et al. | |
| 2006/0195010 A1 | 8/2006 | Arnal et al. | |
| 2006/0195011 A1 | 8/2006 | Arnal et al. | |
| 2008/0132754 A1 | 6/2008 | Thierfelder et al. | |
| 2008/0207988 A1 | 8/2008 | Hanes | |
| 2009/0264871 A1* | 10/2009 | Merced-O'Neill | A61B 17/00008 606/1 |
| 2010/0174134 A1 | 7/2010 | Anderson et al. | |
| 2010/0256442 A1 | 10/2010 | Ogdahl et al. | |
| 2010/0298630 A1 | 11/2010 | Wignall | |

FOREIGN PATENT DOCUMENTS

| | | |
|---|---|---|
| WO | WO 2007/097994 | 8/2007 |
| WO | WO 2007/149348 | 12/2007 |
| WO | WO 2008/057261 | 5/2008 |
| WO | WO 2009/017680 | 2/2009 |
| WO | WO 2010/093421 | 8/2010 |
| WO | WO 2011/082350 | 7/2011 |

OTHER PUBLICATIONS

First Examination Report for Australian Application No. 2016203812, dated Apr. 23, 2017, 5 pages.

Japanese Office Action for Japanese Application No. 2014-509487, dated Oct. 18, 2016, 5 pages.

* cited by examiner

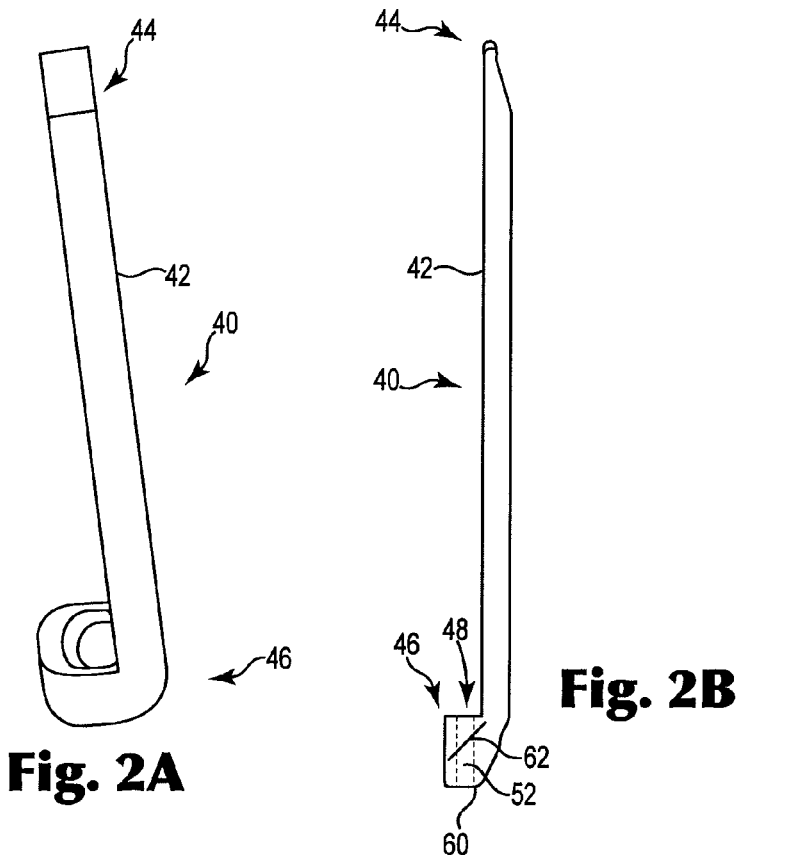
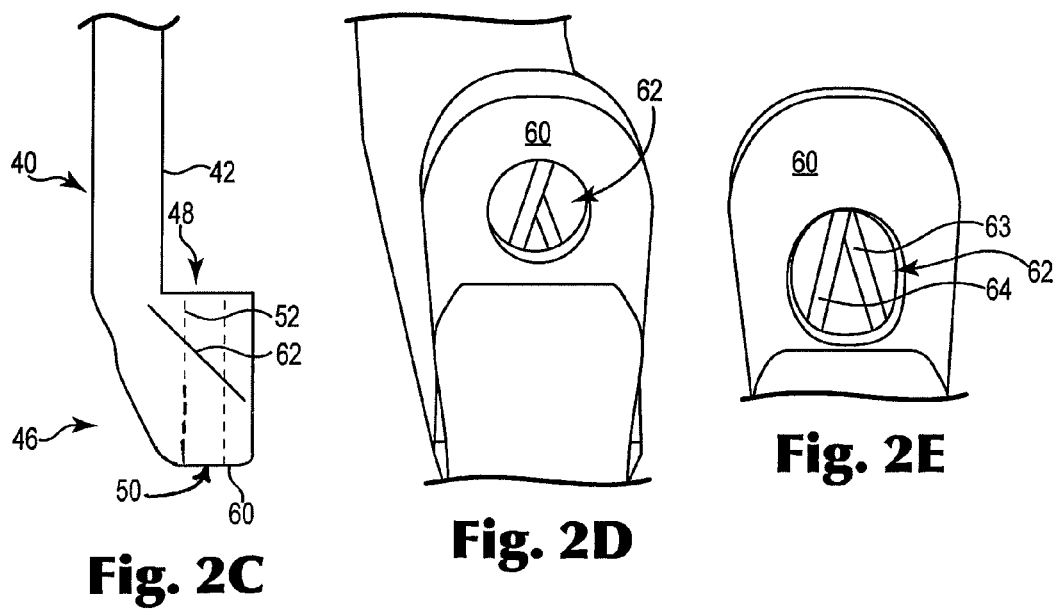
Fig. 2A
Fig. 2B
Fig. 2C
Fig. 2D
Fig. 2E

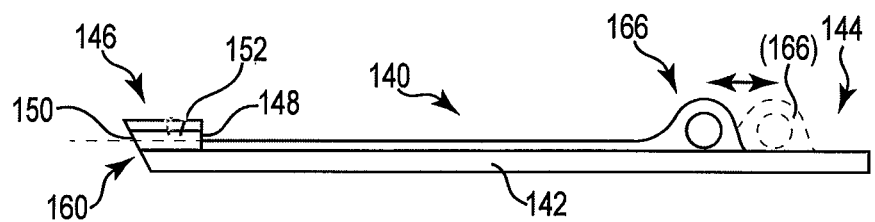
Fig. 3A
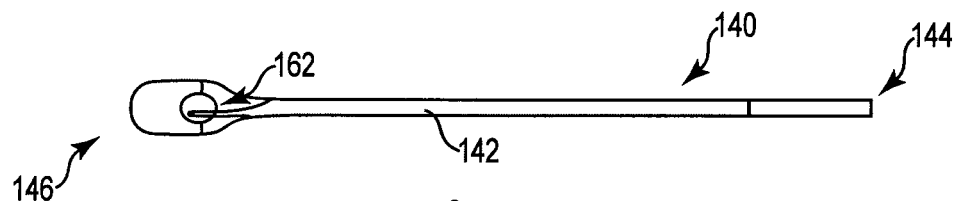
Fig. 3B
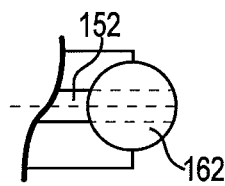 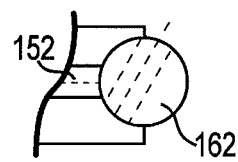
Fig. 3C Fig. 3D

IMPLANTS, TOOLS, AND METHODS FOR TREATMENT OF PELVIC CONDITIONS

CROSS REFERENCE TO RELATED APPLICATION

This application claims the benefit from International No. PCT/US2012/036575, which was granted an International filing date of May 4, 2012, which in turns claims priority under 35 U.S.C. § 119(e) of U.S. Provisional Patent Application No. 61/482,430, filed May 4, 2011 and titled "Tools and Methods for Treatments of Pelvic Conditions", and U.S. Provisional Application No. 61/496,127, filed Jun. 13, 2011 and titled "Implants, Tools, and Methods for Treatment of Pelvic Conditions", which applications are incorporated herein by reference in their entireties.

FIELD OF THE INVENTION

The present invention relates to tools and related methods for treating pelvic conditions by use of a pelvic implant to support pelvic tissue. The pelvic treatments include, for example, treatment of vaginal prolapse by laparoscopic, abdominal, and transvaginal procedures.

BACKGROUND

Pelvic health for men and women is a medical area of increasing importance, at least in part due to an aging population. Examples of common pelvic ailments include incontinence (e.g., fecal and urinary incontinence), pelvic tissue prolapse (e.g., female vaginal prolapse), and other conditions that affect the pelvic floor. Pelvic disorders such as these can be caused by weakness or damage to normal pelvic support systems. Common etiologies include childbearing, removal of the uterus, connective tissue defects, prolonged heavy physical labor, and postmenopausal atrophy.

In more particularity, pelvic floor disorders include cystocele, rectocele, and prolapse such as anal, uterine, and vaginal vault prolapse. Vaginal vault prolapse is a condition that occurs when the upper portion of the vagina loses its normal shape and moves downwardly into the vaginal canal. In its severest forms, vaginal vault prolapse can result in the distension of the vaginal apex outside of the vagina. Vaginal vault prolapse may occur alone, such as can be caused by weakness of the pelvic and vaginal tissues and muscles, or can be associated with a rectocele, cystocele and/or enterocele. A rectocele is caused by a weakening or stretching of tissues and muscles that hold the rectum in place, which can result in the rectum moving from its usual location to a position where it presses against the back wall of the vagina. A cystocele is a hernia of the bladder, usually into the vagina and introitus. An enterocele is a vaginal hernia in which the peritoneal sac containing a portion of the small bowel extends into the rectovaginal space. All of these conditions can represent challenging forms of pelvic disorders for surgeons to treat, which treatment procedures can involve relatively lengthy surgical procedure times. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair vaginal vault prolapse by suturing the vaginal vault (e.g., by stitches) to the supraspinous ligament or by attaching the vaginal vault through mesh or fascia to the sacrum.

There is ongoing need to provide physicians with improved methods and associated instruments for treating pelvic conditions including incontinence, vaginal prolapse (e.g., vaginal vault prolapse), and other pelvic organ prolapse conditions, wherein such methods can include those that are minimally invasive, safe, and highly effective.

SUMMARY

Tools, systems, and methods as described herein can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies, and the like. In accordance with the invention, sacral colpopexy procedures can be performed through an abdominal opening, laparoscopically, or transvaginally, which procedures will require different approaches, each of which can use certain embodiments of devices and/or methods of the invention In a sacral colpopexy procedure it is desirable to simplify the procedure so the surgeon is not overwhelmed. Recently, multi-piece implants have been developed for supporting vaginal tissue. These multi-piece implants can include at least two pieces (e.g., an extension portion piece and support portion piece) engaged with each other at an adjustment area or feature. Other implants can include those that are Y-shaped, which include a base member and two support members extending from the base member, wherein the attachment of portions of the Y-shaped implant can be adjustable relative to their respective attachment points within a patient (e.g., the sacrum). Devices or tools of the invention described herein can be referred to as adjusting and cutting tools, which provide methods for adjusting this engagement between two pieces of an adjustable implant or between an implant and an anchor or attachment point, and then also cutting a portion of the implant with the same tool. Useful features of these adjusting and cutting tools can include a shaft that extends between a proximal end and a distal end, where the proximal end can be manipulated outside of the patient and the distal end includes an adjusting feature that can contact two pieces of the implant to allow adjustment between the two pieces. The distal end also includes a cutting mechanism to allow the distal end to be used to cut a component of the implant.

Various surgical tools, implants, and procedural improvements are also disclosed herein that involve separate tensioning to the anterior and posterior compartments in a sacral colpopexy procedure, and may additionally involve single arm tensioning to prevent or minimize twisting. Certain embodiments of methods and implants described herein involve the use of a Y-shaped mesh component that is designed to fixate to the sacral promontory, and may additionally include two apical mesh pieces that are sutured to the anterior and posterior vaginal walls. Embodiments of implants and methods can involve placement of an implant to support pelvic tissue, by way of an incision of minimum size.

Certain embodiments relate generally to fixation or attachment devices ("anchors") and related methods for placing a pelvic mesh implant, and methods for treating pelvic conditions such as incontinence, vaginal prolapse, and other conditions caused by muscle and ligament weakness. Embodiments of the implants can include a tissue support portion and one or more anchors, arms and the like.

In addition, disclosed are combination devices (implants, tools, and anchors, etc.) and related methods useful for anterior or posterior prolapse repair with other treatments for pelvic floor disorders such as urinary incontinence, pelvic floor decent (levator avulsion), and/or sacral fixation. Exemplary levator and support devices can be introduced through a vaginal incision to tie in with conventional transvaginal mesh repairs and other applications, or can be introduced abdominally (e.g., laparoscopically). After implantation, an adjusting or cutting tool can be used to optimize the length and/or positioning of components relative to each other.

BRIEF DESCRIPTION OF THE DRAWINGS

The present invention will be further explained with reference to the appended Figures, wherein like structure is referred to by like numerals throughout the several views, and wherein:

FIG. 2A is a perspective view of an embodiment of an adjusting and cutting tool in accordance with the invention;

FIG. 2B is a side view of the tool of FIG. 2A;

FIG. 2C is an enlarged view of a distal end of the tool of FIGS. 2A and 2B;

FIG. 2D is an end view of the distal end of the tool illustrated in FIG. 2C;

FIG. 2E is an end view of the distal end of the tool illustrated in FIG. 2C, taken from the opposite direction from the end view of FIG. 2D;

FIG. 3A is a side view of an embodiment of an adjusting and cutting tool in accordance with the invention;

FIG. 3B is a top view of the tool of FIG. 3A;

FIGS. 3C and 3D are enlarged views of a distal end of the tool illustrated in FIGS. 3A and 3B, with a rotating cutting blade in a neutral position and in a cutting position, respectively;

DETAILED DESCRIPTION

Figure 1:
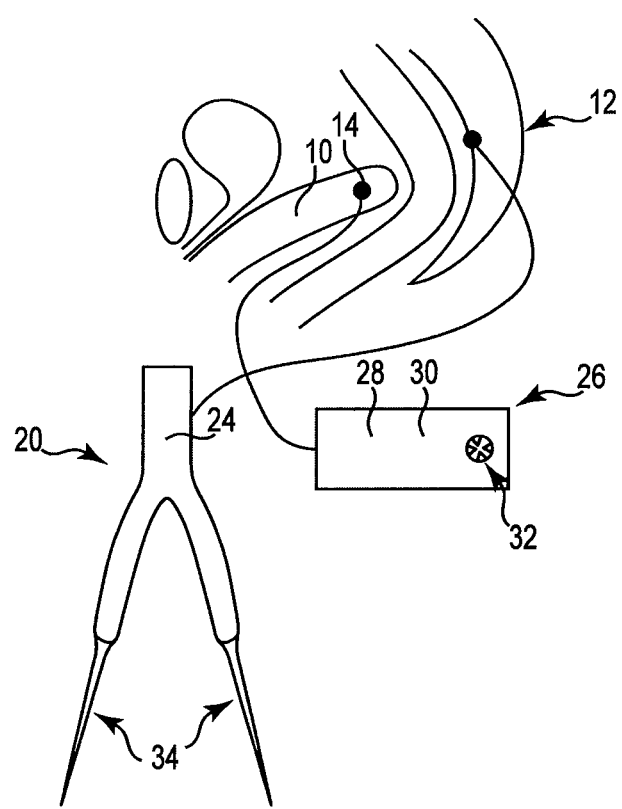
FIG. 1 is a schematic view of a Y-shaped implant as it can be positioned relative to a patient's anatomy.
Figure 4A:
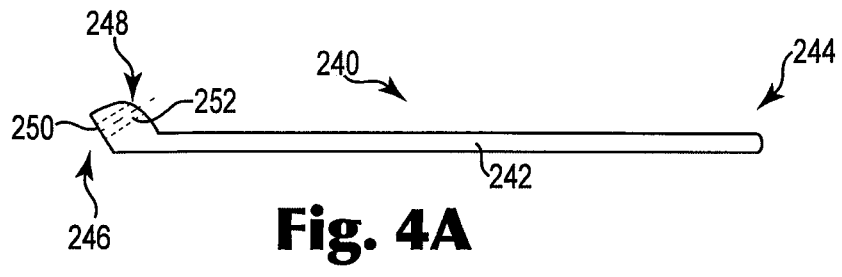
FIG. 4A is a side view of an embodiment of an adjusting and cutting tool in accordance with the invention.
Figure 4C:
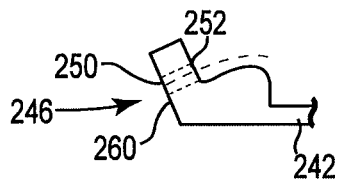
FIGS. 4C and 4D are side views of the distal end of the adjusting and cutting tool of FIG. 4A.
Figure 4B:
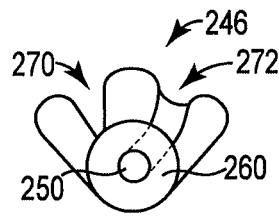
FIG. 4B is an end view of the distal end of the tool illustrated in FIG. 4A.
Figure 4D:
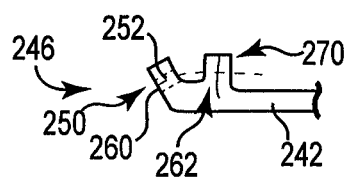

The methods and tools as described can be useful in procedures for supporting vaginal tissue, including but not limited to sacral colpopexy procedures (e.g., transvaginal and abdominal), along with procedures for treating vaginal vault prolapse caused by rectocele, cystocele, enterocele, and other causes. A sacral colpopexy is a procedure for providing vaginal vault suspension, which can be accomplished with the use of an implant such as a strip of mesh or other material—of posterior vaginal tissue (e.g., a vaginal cuff) to a region or component of sacral anatomy such as the sacrum (bone itself), a nearby sacrospinous ligament, uterosacral ligament, or anterior longitudinal ligament at the sacral promontory, such as may be accomplished using bone screws that are implanted into the sacrum. Sacral colpopexy may be performed through an abdominal incision, a vaginal incision, or laparoscopically. An implant such as a synthetic mesh can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

Many of the implants discussed herein include the use of an anchor, as will be described in further detail relative to the present invention. As used herein, the term "anchor" refers non-specifically to any structure that can connect an implant to tissue of a pelvic region. The tissue may be bone or a soft tissue such as a muscle, fascia, ligament, tendon, or the like. Certain methods, implants, and anchors of the present description incorporate a helical anchor such as a screw or coil that can be inserted (e.g., driven) into tissue, preferably soft tissue such as an anterior longitudinal ligament, by rotating about a longitudinal axis upon which the helical anchor advances into the tissue in a longitudinal direction. Other methods may include an anchor in the form of a "self-fixating tip," which can be inserted by pushing the anchor using a straight or curved needle.

An embodiment of the invention is directed generally to surgical instruments, assemblies, and implantable articles for treating pelvic floor disorders such as various forms of prolapse. According to embodiments described herein, a surgical implant can be used to treat a pelvic condition, including the specific examples of surgically placing a surgical implant to treat a pelvic condition such as vaginal vault prolapse. Described herein are various features of surgical implants, surgical tools, surgical systems, surgical kits, and surgical methods useful for installing implants.

One embodiment of an implant that can be used to treat such pelvic disorders is an implant that includes a tissue support portion used to support pelvic tissue such as vaginal tissue, along with one or more extension portions. During use, the tissue support portion can be placed in contact with and attached to tissue to be supported, such as through the use of sutures. An implant of this type can additionally include one or more extension portions attached to the tissue support portion. Optionally a tissue fastener (e.g., a soft tissue anchor or self-fixating tip) can be included at an end of an extension portion, with the tissue fastener and extension portion(s) being designed to attach to tissue in the pelvic region to secure the distal end of the extension portion to the tissue.

The tissue support portion of the above-described implant is designed to support a specific portion of vaginal tissue (anterior, posterior, apical, etc.), depending on the defect that is to be corrected. The tissue support portion can be sized and shaped to contact the desired tissue when installed, (e.g., as a "sling" or "hammock"), to contact and support vaginal tissue. A tissue support portion that is located between two or more extension portions may be refereed to as a "central support portion" or a "support portion." The tissue support portion may comprise a number of different materials, such as tissue (e.g., porcine tissue), mesh, or other materials or combinations of materials.

Extension portion(s) of the above-described implant can be elongate pieces of material that extend from the tissue support portion and are useful to pass through or attach to tissue of the pelvic region to thereby provide support for the tissue support portion and the supported tissue. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip or another form of tissue fastener) to thereby provide support for the tissue support portion and the supported tissue. One or more extension portions can extend from a tissue support portion for attachment to tissue in the pelvic region, such as by extending through a tissue path to an internal anchoring point (for attachment by bone anchor, tissue fastener, etc.), or to an external incision.

An extension portion piece can be connected at one end by an anchor (e.g., a self-fixating tip or a helical anchor) to tissue of a pelvic region, such as at a component of sacral anatomy. A second end of the extension portion piece can be connected by way of an adjusting engagement, to the support portion piece. The adjusting engagement may include a frictional engagement element such as a grommet, a one-way or a two-way frictional adjusting element, or the like. The support portion piece, in turn, can contact and support tissue, such as vaginal tissue, in treating vaginal prolapse.

Exemplary implants can be made of materials and may be generally shaped and sized according to previous implants, but modified to include features as described herein, such as a frictional adjusting element, multi-piece construction, a multi-layer tissue support portion, etc. For example an implant can have features as described in the following exemplary documents: U.S. patent application Ser. No. 10/834,943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International Patent Application No. PCT/US2006/028828, having an International Filing Date of Jul. 25, 2006; the entireties of each of these disclosures being incorporated herein by reference.

Exemplary implants can be made of materials and exhibit general size and shape features that might be similar to those sold commercially by American Medical Systems, Inc., of Minnetonka Minn., under the trade names "Apogee", "Perigee", and "Elevate" for use in treating pelvic prolapse (including vaginal vault prolapse, cystocele, enterocele, etc.). In addition, these implants can include portions or sections that are synthetic and/or made of biological material (e.g., porcine, cadaveric, etc.). Extension portions, which may be made of a single piece of material or of multiple pieces of material, may be a synthetic mesh, such as a polypropylene mesh, while the tissue support portion may be synthetic (e.g., a polypropylene mesh) or biologic.

Types of exemplary implants that can be generally useful as discussed herein can include those previously and currently used in treating pelvic conditions, including those implants referred to "slings," "strips," "mesh strips," "hammocks," among other terms for pelvic implants. Particular examples of implants for treating vaginal prolapse can include a central support portion and from two to four to six extension portions, and may take the form of an integral piece of mesh or multiple pieces of mesh attached in a modular fashion. See, e.g., Assignee's copending U.S. patent application Ser. Nos. 11/398,369; 10/834,943; 11/243, 802; 10/840,646; PCT/2006/028828; among others.

Another embodiment of an implant that can be used to treat certain pelvic disorders in accordance with the invention is an implant that includes a preassembled implantable article, which can reduce challenges faced by a surgeon by eliminating the need to create a customized implantable article for surgical procedures. One particular embodiment is an implant that is preassembled into a Y-shape that includes a base portion and a head portion, wherein the head portion comprises first and second tissue engagement portions, each of which extends from the base portion. The first and second tissue engagement portions can be secured to the base portion using a wide variety of configurations and materials, such asusing a configuration that distributes forces that would otherwise tend to separate one or both of the tissue engagement portions from the base portion. Such a configuration may include the use of biocompatible materials such as tissue adhesives, tissue sealants, biocompatible bonding agents (e.g. silicone), and biocompatible adhesives. Alternatively, RF or ultrasonic welding or heat sealing may be used alone or in conjunction with other techniques to create a separation force distribution means.

In an embodiment of a preassembled implant, the implant can include a plurality of pores that afford tissue ingrowth and resist infection, and can include a backing that is coated. The backing material may include one or more woven, knitted or inter-linked filaments or fibers that form multiple fiber junctions, and/or may include monofilament and multifilament embodiments. The fiber junctions may be formed via weaving, bonding, ultrasonic welding, knitting or other junction forming techniques, including combinations thereof. In addition, the size of the resultant openings or pores of the implantable article should be sufficient to allow tissue in-growth and fixation within surrounding tissue.

The preassembled implant may be made of a variety of materials including, but not limited to, Prolene™, nylon, polypropylene, Deklene™, poly-L-lactide (PLLA), polyethylene glycol (PGA), polyester and any combination of materials. Depending on the desired treatment, the implant or portions thereof, may be absorbable, non-absorbable and/or resorbable. Non-synthetic structures are also included within the scope of the invention. Other synthetic and non-synthetic materials suitable for use for the implants include, but are not limited to, synthetic biomaterials, allografts, homografts, heterografts, autologous tissues, materials disclosed in U.S. Provisional Applications Ser. No. 60/263,472, Ser. No. 60/281,350 and Ser. No. 60/295,068 (the contents of which are incorporated herein by reference), synthetic materials (such as metallics, polymerics, and plastics) and any combination of such materials. Specific examples of suitable synthetic materials that can be used include, but are not limited to, polypropylene, polyester, polyethylene, nylon, PLLA and PGA. The material can generally be selected from materials that cause minimal to no reaction with body tissues and fluids and that will retain its particular material characteristics/properties indefinitely or for a predetermined length of time. Portions or all of the material may be resorbable if consistent with the desired surgical procedure.

Dimensions of any of the implants of the invention can be as are determined to be useful for any particular installation procedure, treatment, patient anatomy, and to support a specific tissue or type of tissue. Exemplary dimensions can be sufficient to allow the tissue support portion to contact tissue to be supported, and to allow extension portions to extend from the tissue support portion to a desired anatomical location to allow the extension portion to be secured to or pass through tissue of the pelvic region and support the tissue support portion.

A distal end of an extension portion, according to embodiments of the invention, can include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. The implant may also have extension portions that do not include a tissue fastener at a distal end of an extension portion, for example if the distal end is designed to be secured to tissue by other methods (e.g., suturing), or is intended to pass through an external incision. During installation of the implant, the tissue fastener can be secured to any desired tissue, for example fibrous tissue such as a muscle, a ligament and/or its surrounding tissue, or a tendon and/or its surrounding tissue; or tissue at or near the ischial spine.

In an exemplary implantation procedure for an implant that includes a tissue portion and one or more extension members, a portion of the implant, such as an extension portion, can be placed at and passed through soft support tissue of the pelvic region, to lead and pass the extension portion through the soft support tissue. The soft support tissue can be any tissue desired or useful to which to attach an extension portion, for example any of the following: muscle tissue of an obturator foramen (e.g., obturator internus muscle), tissue of an arcus tendineus or surrounding an arcus tendineus, tissue of a sacrospinous ligament, tissue in a region of a sacrospinous ligament, tissue of a coccyx region, tissue of a region of an ischial spine, tissue of coccygeous muscle, tissue of iliococcygeous muscle, tissue of a uterosacral ligament, tissue of levator muscle, or combinations of these. Tissue in a "region" of an ischial spine can be tissue that is within one centimeter of an ischial spine, including tissue of the levator ani muscle (e.g., iliococcygeous muscle) and arcus tendineus.

When placing an extension portion through soft support tissue, embodiments of the invention can lead the extension portion into the a surface of soft support tissue at an insertion location, pass the extension portion through a mass of one or more types of soft support tissue, then exit the soft support tissue at an exit location on the surface of soft support tissue. The insertion location and the exit location can both be located at surfaces of a single side of tissue, generally at surfaces on the side of the tissue that can be accessed within the pelvic region, e.g., from a perineal incision, a vaginal incision, or an abdominal incision. In other words, the extension portion enters on one side of tissue (generally on the side within the pelvic region), passes laterally or "tunnels" through a length of soft support tissue, then exits in the direction substantially opposite of the direction of insertion, returning into the pelvic region. The extension portion does not traverse soft support tissue by entering into one side of tissue, traversing the thickness of the tissue, and exiting the other side.

According to certain embodiments, the insertion and exit locations, at tissue surfaces on the same side of tissue, can be at surfaces of the same tissue, e.g., if both of the insertion and exit locations are located at surfaces of the same muscle, ligament, or tendon. For example, the extension portion enters soft support tissue at a surface on one side of coccygeus muscle; the extension portion passes laterally through a length of coccygeus muscle, e.g., tunneling sideways or laterally through the muscle; and the extension portion then exits the coccygeus muscle through an exit location at a surface on the same side of the muscle as the insertion location. Alternately, the extension portion can enter soft support tissue at a surface on one side an obturator internus muscle; the extension portion can pass laterally through obturator internus muscle, e.g., tunneling sideways or laterally through the muscle; and the extension portion can then exit the obturator internus muscle through an exit location at a surface on the same side of the obturator internus muscle as the insertion location.

According to other embodiments of the invention, the exit location and the insertion location can be located on nearby, adjacent, or proximate locations of nearby or neighboring tissues, e.g., adjacent surface of different muscle, ligament, tendon, or combinations of these. For example, the extension portion can enter soft support tissue at a surface on one side of coccygeus muscle; the extension portion can pass through the coccygeus muscle, e.g., tunneling sideways or laterally through the muscle and to a location behind a sacrospinous ligament; the extension portion can then exit the at a surface of the sacrospinous ligament through an exit location on the side of the ligament that is adjacent to the insertion location on the coccygeus muscle.

Another example of a location for attaching an end of an extension portion is at a tissue path that passes through, or terminates at, a coccyx region as described in Applicant's copending U.S. patent application Ser. No. 11/398,368, filed Apr. 5, 2006, the entirety of which is incorporated herein by reference. That application describes the use of an implant to treat vaginal prolapse (e.g., vault prolapse, enterocele, cystocele, rectocele) using an implant that includes a tissue support portion and extension portions, wherein extension portions are passed through a tissue path that includes a region of the coccyx bone (i.e., a "coccyx region" or a "transcoccyx" tissue path).

Exemplary methods involve placement of a support member to support prolapsed tissue, including placement of an extension portion of the support member at coccyx region, proximal to the coccyx bone, e.g., attached to or extending through muscle (e.g., ischiococcygeous muscle, iliococcygeous muscle), or ligament (sacrospinous ligament) lateral to the coccyx bone. Exemplary tissue paths can initiate from a region surrounding vaginal vault tissue and can extend past the rectum to a location proximal to the coccyx bone. An extension portion of the support member can generally be guided through such a passage prepared in muscle or other tissue, past the rectum, proximal to the coccyx bone, and attached to tissue internally in this region. A distal end of an extension portion can attach to any tissue of the coccyx region, such as with a tissue fastener securing a distal end of extension portion to muscle or ligament (e.g., sacrospinous ligament) in the coccyx region. Alternately, the distal end of extension portion can extend through tissue of the coccyx region and to an external incision of the epidermis.

As described elsewhere herein, a length of an extension portion (extended through any tissue path) can optionally be fixed or adjustable, allowing a surgeon to alter the length of an extension portion before, during, or after implantation. On the other hand, adjustment and tensioning mechanisms can also be excluded from embodiments of implants or from particular extension portions, e.g., superior extension portions that will attach to an obturator foramen, or extension portions that will be placed at a tissue path extending to an external incision.

Referring now to the Figures, FIG. 1 generally illustrates an exemplary implant, tool, and method related to providing support for an apex of a vagina 10 by fixation and support from a component of sacral anatomy, using an adjustable implant. This embodiment comprises a Y-shaped implant 20 having a posterior portion 24 for attaching to a sacrum (i.e., a component of sacral anatomy such as an anterior longitudinal ligament) that is generally designated by reference numeral 12, and two mesh or polymeric rod arms 34 that can be can be routed through an aperture (e.g., a locking eyelet 32) on each of two anterior or support portions 26, which are attachable to vaginal wall tissue to support a vaginal apex. An exemplary attachment area to the vagina 10 is indicated by point 14. Anterior or support portions 26 include an anterior area 28 for attachment to a vaginal wall and a posterior area 30 that includes an eyelet 32 for adjustably engaging one each of the two arms 34. With implant 20 secured to a component of sacral anatomy, and each of anterior support portions 26 attached to vaginal wall tissue, each arm 34 can be led through one of eyelets 32. A tool, such as an adjusting and cutting tool of the invention, can then be used to push the eyelet 32 up the arm 34 and attached mesh, until a specific tension has been reached. Such a tool can then cut off any undesired, excess length of arm 34 or attached mesh material.

An exemplary embodiment of an adjusting and cutting tool 40 of the invention for use in a method such as positioning an adjustable implant to support vaginal tissue (e.g., such as can be accomplished in a sacral colpopexy procedure), is illustrated generally in FIGS. 2A-2E. Cutting tool 40 includes a distal end that includes both a cutting structure and an adjusting structure that can be placed at a useful location, such as near vaginal tissue, such as tissue of a vaginal vault. Such an adjusting and cutting tool can be an elongate tool that is configured generally as illustrated or that can be differently shaped or sized, but that in any case generally includes a distal end that engages an elongate portion of an implant (e.g., an elongate mesh or rod portion of an extension portion piece of an adjustable multi-piece implant) to allow manipulation of the elongate portion, for adjustment and cutting of the elongate portion after adjustment. Advantages of such an adjusting and cutting tool can include safe and controlled cutting action of a portion of an implant, preventing tissue damage and trauma; and a controlled cut that can ensure a desired length of implant remaining at the adjusting engagement.

FIGS. 2A and 2B illustrate views of exemplary adjusting and cutting tool 40. Tool 40 generally includes an elongate member 42, a proximal end 44, and a distal end 46. As is shown in FIG. 2C, which is an enlarged view of the distal end 46 of cutting tool 40, distal end 46 includes a channel 52 extending from a distal channel opening 50 to a proximal channel opening 48. Channel 52 is shown as being generally straight in the figures, although it is contemplated that the channel 52 can instead be angled or curved in such a way that the distal and proximal channel openings 50, 48 will be offset relative to each other. In any case, the channel openings and the channel itself are sized to have an inner diameter that is larger than the material that will be inserted therein. Dimensions of channel 52 and proximal and distal apertures 48 and 50 can be useful to engage an elongate portion or piece of an implant. Channel 52 may define an opening having a diameter in a range from 0.5 to 1.2 centimeters (e.g., from 0.5 to 1.0 centimeter), for example, depending on the size of the material that will be inserted therein.

Distal end 46 further includes a blade 62 (described below in further detail) positioned with at least one of its cutting surfaces extending into the channel 52. The blade 62 will be used for cutting an elongate portion of implant that is passed through channel 52. In use, an elongate portion or piece of an adjustable implant (e.g., mesh or a polymeric rod of an extension portion piece, which can be referred to as a first piece of the implant) can be threaded or pushed/pulled through channel 52 and moved proximally or distally to adjust the location of the elongate portion or piece relative to another piece of the adjustable implant (e.g., a support portion piece). A distal surface 60 of distal end 46 can be used to apply pressure to a second component or piece of the adjustable implant (e.g., an adjusting engagement such as a grommet, eyelet, mesh, or a support portion piece) to move the second component or piece relative to the elongate portion or piece of the implant threaded through channel 52. The first (extension portion) piece may have previously been secured to tissue of the pelvic region, and the second (support portion) piece may be secured to vaginal tissue, such that moving the first piece relative to the second piece can also adjust the position of the vaginal tissue, tension in the first and second pieces, or both. Upon desired adjustment of the implant, tool 40 can be manipulated (e.g., pulled proximally) which will cause the blade 62 to cut the elongate portion or piece of the adjustable implant at a location on a proximal side of the second (support portion) piece.

According to one embodiment illustrated best in FIG. 2C, channel 52 can be relatively straight or cylindrical, but can optionally be designed with a pair of turns or corners that create a "jog" that separates two straight portions that are proximal and distal to the pair of turns. Alternatively, channel 52 may include one or more curved portions, more than two straight portions, and/or other configurations. If the channel includes a single jog, blade 62 can be located at a proximal turn of the channel, for example.

An exemplary embodiment of blade 62 is illustrated in FIGS. 2D and 2E, where such a blade is positioned and configured to provide one or more cutting surfaces that can cut the implant in a desired location. Optionally (and as illustrated), blade 62 includes two cutting surfaces 63, 64, which are arranged at an angle relative to each other. This may be accomplished with a blade that itself includes multiple cutting surfaces, or by providing a blade that is actually a multi-component blade assembly. Although the illustrated embodiment shows these cutting surfaces 63, 64 as coming together at a V-shaped intersection, the surfaces 63, 64 can instead be arranged differently relative to each other. It is further contemplated that the blade 62 can instead include more or less than two cutting surfaces. In any case, the cutting surfaces can be provided with a uni-directional chamfer or tapered surface such that a material can be slid in one direction over the cutting surface(s) without damaging the material, but when the material is slid in the opposite direction relative to the cutting surface(s), the material will be severed by one or more sharp surfaces. In this way, the material can be adjusted without damage prior to cutting the material.

Blade 62 can be oriented at a non-perpendicular and non-parallel angle relative to elongate member 42, in order to orient cutting surfaces 63, 64 so that they face toward proximal end 44. FIG. 2C shows a side view of distal end 46 of tool 40, including blade 62 oriented at an exemplary angle of about 45 degrees relative to shaft 42. This angle of blade 62 relative to shaft 42 can vary (e.g., from between 30 and 60 degrees, or from 20 to 70 degrees), as desired to provide a desired cutting capability to the tool 40. With this embodiment, an elongate portion of implant can be threaded through channel 52 so that distal end 46 will be capable of moving distally along the elongate portion of implant without cutting the implant, and then will be capable of moving proximally to cause cutting surfaces 63, 64 to engage and cut the elongate portion of implant. Thus, with cutting surfaces 63, 64 facing proximally, as illustrated, tool 40 can be moved proximally toward the user to cause at least one of cutting surfaces 63, 64 to engage and sever through the elongate portion of implant, which can be done while placing tension on the elongate portion of implant. In addition, tool 40 can be moved distally away from the user, so that cutting surfaces 63, 64 will not engage or cut the elongate portion of implant. Blade 62 can optionally be removable and replaceable from the tool 40, and can also include a cover or other feature that secures the blade in its desired position, and/or the blade can be otherwise secured in its desired position within the tool 40, such as with a friction fit, adhesives, or the like.

In an alternative embodiment, tool 40 can further include an adjusting feature at its proximal end 44 that includes a channel or opening that does not include a cutting feature such as blade 62. Such an adjusting feature may be provided on a flange or extension that extends from the proximal end 44, for example.

FIGS. 3A and 3B illustrate, among other things, a side view and a top view, respectively, of another exemplary adjusting and cutting tool 140 for adjusting and cutting an elongate portion or piece of an adjustable (e.g., multi-piece) implant in an implant attachment and adjustment procedure. Tool 140 includes elongate member 142, a proximal end 144, and a distal end 146. Distal end 146 includes a channel 152 extending between a distal aperture 150 and a proximal aperture 148. Channel 152 can be used by placing (e.g., threading) an elongate portion or piece of an adjustable implant (e.g., mesh or polymeric rod) through channel 152 and moving the portion proximally or distally to adjust the location of a (first) elongate portion or piece relative to another (second) piece of the adjustable implant (e.g., a support portion piece). Channel 152 also includes a blade 162 as part of a rotary cutting head, which can be used for cutting an elongate portion or piece of implant that is positioned within channel 152.

Tool 140 also includes an actuator 166 adjacent to the proximal end 144 of elongate member 142, wherein the actuator 166 is shown in both actuated and resting positions in FIG. 3A. Actuator 166 is shown as including a finger grip portion that can be moved proximally and distally to actuate or move blade 162 to selectively cut an elongate portion of implant located within channel 152, when it is desired to do so. In particular, an elongate portion of an implant (e.g., an extension portion piece) may be threaded through channel 152. A distal surface 160 of distal end 146 can be used to apply pressure to a second (different) component or piece of the adjustable implant (e.g., an adjusting engagement such as a grommet, eyelet, mesh, or a support portion piece) to move the second component or piece relative to the (first) elongate portion or piece of the implant threaded through channel 152. Upon desired lengthwise adjustment of the implant (and tissue, e.g., vaginal tissue), actuator 166, which is operably attached to blade 162, can be manipulated (e.g., pulled proximally or pushed distally) to cause blade 162 to be reoriented from a non-cutting position (see FIG. 3C) to a cutting position (see FIG. 3D) in which it can sever or cut the elongate portion or piece of the adjustable implant at a desired location relative to channel 152.

FIGS. 4A-4D illustrate another exemplary embodiment of an adjusting and cutting tool 240, which can be used for adjusting and cutting an elongate portion or piece of an adjustable implant in implantation procedure. Tool 240 includes an elongate member 242, a proximal end 244, and a distal end 246. Distal end 246 includes a channel 252 extending from a distal aperture 250 to a proximal aperture 248. When viewed from the end, as in FIG. 4B, distal end 246 is further illustrated as including a cutting slot 270 and at least one adjustment groove 272. Tool 240 can be used by placing (e.g., threading) an elongate portion or piece of an adjustable implant (e.g., mesh) through channel 252 and adjustment groove 272, and moving the elongate portion or piece proximally or distally to adjust the location of the elongate portion or piece relative to another (second) piece of the adjustable implant (e.g., a support portion piece). Channel 252 also communicates with cutting slot 270, which includes a cutting blade 262 that is used for cutting an elongate portion of implant that is passed through channel 252 and cutting slot 270.

When the elongate portion or (first) piece of implant is placed in the adjustment groove 272, a distal surface 260 of distal end 246 can be used to apply pressure to a different component or second piece of the adjustable implant (e.g., an adjusting engagement such as a grommet, eyelet, mesh, or a support portion piece) to move the component or second piece relative to the (first) elongate portion or piece of the implant threaded through channel 252. After the implant is adjusted, the implant material that is threaded through channel 252 at distal end 246 can be moved laterally relative to distal end 246, to cutting slot 270, where blade 262 can cut the elongate portion or piece of the adjustable implant.

Figure 5A:
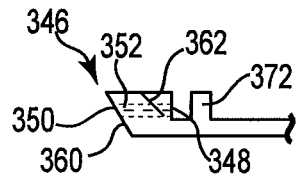
FIG. 5A is a side view of a distal end of an embodiment of an adjusting and cutting tool in accordance with the invention.
Figure 5B:
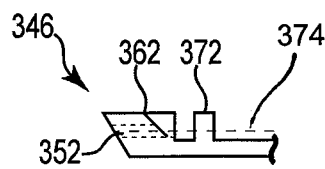
FIG. 5B is a side view of the distal end of the tool portion shown in FIG. 5A, illustrating a length of material as it can be positioned during an adjustment procedure.
Figure 5C:
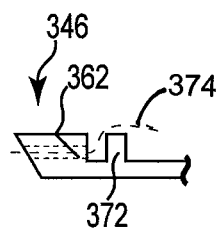
FIG. 5C is a side view of the distal end of the tool portion shown in FIG. 5A, illustrating a length of material as it can be positioned during a cutting procedure.

FIGS. 5A-5C illustrate a distal end 346 of another version of a tool that includes a distal end with a cutting feature and an adjusting feature that can be used separately to adjust and then cut an elongate portion or piece of implant. Referring to FIG. 5A, distal end 346 includes a channel 352, a distal aperture 350, a proximal aperture 348, a distal surface 360, a blade 362, and a "tower" or "elevator" 372 in the form of an extended structure that extends laterally near proximal aperture 348 of channel 352. Distal end 346 includes channel (e.g., hole, or aperture) 352 extending from distal aperture 350 to proximal aperture 348. Tower 372 is a structure on a proximal side of aperture 348 that can be used to gain leverage and produce movement of an elongate portion or piece of implant 374 located at distal end 346, passing through channel 352, relative to blade 362, by manipulation of a proximal end of the portion or piece of implant. Blade 362 extends partially into channel 352, and is angled to orient a sharpened cutting edge to face in a proximal direction, allowing an elongate portion or piece of implant 374 to pass freely when moving in a proximal direction relative to blade 362 (e.g., when tool 340 is moved distally). When the elongate portion or piece of implant is leveraged by being manipulated to be placed at tower 372, and tool 340 is moved proximally, the elongate portion or piece of implant 374 will contact the cutting surface of blade 362 and be severed.

Figure 6A:
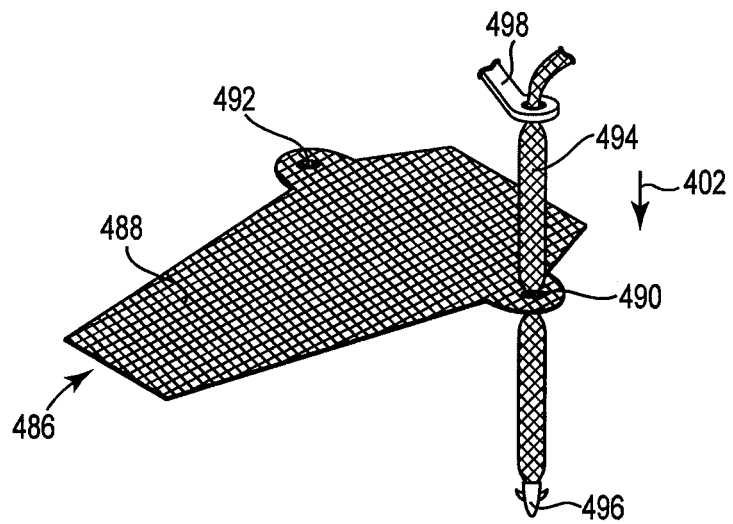
FIGS. 6A and 6B are perspective views of a multi-piece implant and adjustment and cutting tool according to the invention.
Figure 6B:
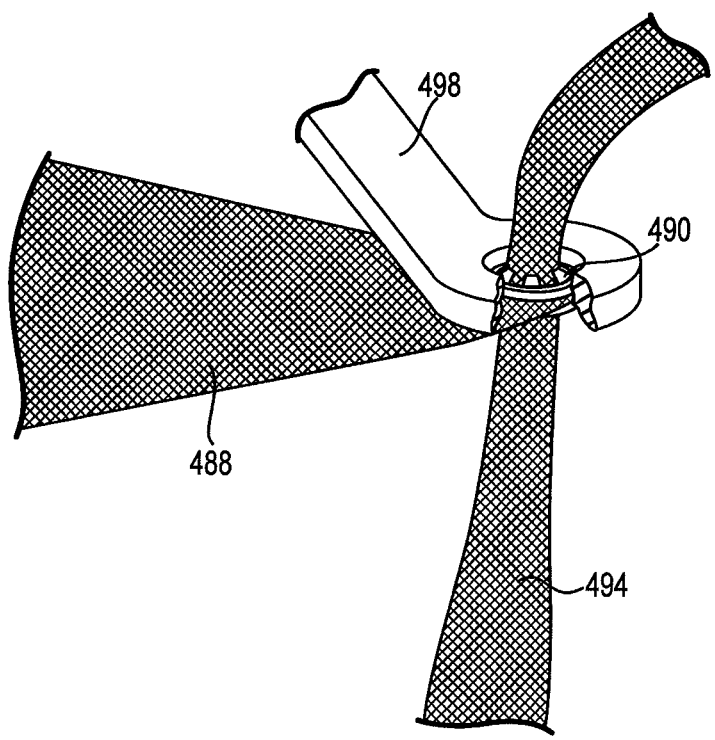

FIGS. 6A and 6B illustrate an exemplary implantation of a multi-piece pelvic implant 486 using an exemplary adjusting and cutting tool 498. It is noted that the end of tool 498 illustrated in this Figure does not necessarily illustrate a particular cutting tool, but instead is a general depiction of a distal end of an adjusting and cutting tool of the invention and how it can be used in an implantation process, where the tool can include any of the cutting features and configurations described above, along with equivalents thereof. In this embodiment, one-way frictional adjusting elements are secured to a support portion piece, and a segment of an extension portion piece is adjustably engaged with the frictional adjusting element. In particular, implant 486 includes a support portion piece 488 having frictional adjusting elements 490 and 492. Frictional adjusting elements 490 and 492 include an aperture through which a segment of extension portion 494 is threaded. Multiple teeth or other features can be located to contact the segment of extension portion 494 passing through the aperture, allowing the segment of extension portion piece to move through frictional adjusting element 490 in one direction, while resisting movement in the opposite direction.

Extension portion piece 494 is shown adjustably connected to frictional adjusting element 490. A segment of extension portion piece 494 extends through frictional adjusting element 490, and tissue fastener 496 (which may include a self-fixating tip, for example) is located at a distal end of extension portion piece 494. Frictional adjusting elements 490 and 492 allow an extension portion piece 494 to move through the frictional adjusting elements in one direction, while resisting movement in the opposite direction, in order to adjust the length extension portions of implant 486, as illustrated, by adjusting the amount of extension portion piece 494 that extends through frictional adjusting element 490 or 492.

An implant of the type illustrated in FIGS. 6A and 6B can be implanted, and then adjusted and cut with the assistance of tool 498 that helps to move one or more portions of the implant relative to each other. Tool 498, as shown, includes a channel or aperture at its distal end that receives extension portion 494. In use, when tip 496 is anchored in tissue, tool 498 can be slid along extension portion piece 494 in an adjustment direction 402 until the distal end of tool 498 contacts the frictional adjusting element 490. Further movement of adjustment tool 498 in adjustment direction 402 can further adjust the distance between the tip 496 and the support portion piece 488 in order to reduce the length of the extension portion of implant 486. At this point, a cutting mechanism of the tool 498 can be activated to cut the extension portion 494 at a desired location, which activation can involve movement of a cutting blade relative to the extension portion, movement of the tool 498 in an opposite direction to cause its blade(s) to cut the extension portion, or another movement that facilitates cutting.

Figure 7:
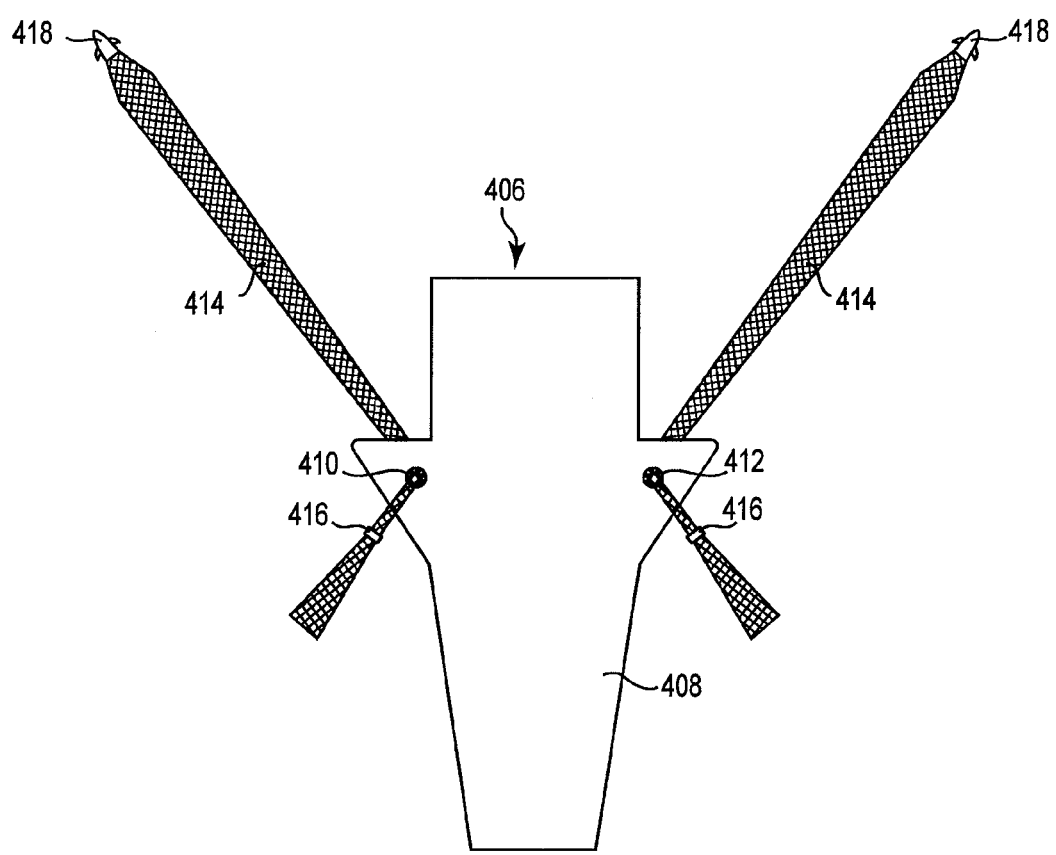
FIG. 7 is a top view of a multi-piece implant and adjustment and cutting tool according to the invention.

FIG. 7 illustrates another exemplary multi-piece pelvic implant 406 that can be adjusted with an adjustment and cutting tool of the invention, embodiments of which are described above. In this embodiment, a frictional adjusting element is moveably engaged along an extension portion piece that extends through an opening of a support portion piece. The placement of the frictional adjusting element can be moved (e.g., in an adjusting direction toward an aperture 412) to adjust the length of the extension portion, e.g., as measured to be the length between the support portion piece and a distal end of the extension portion piece.

Implant 406 includes a support portion piece 408 having loose apertures (e.g., grommets or openings) 410 and 412. Extension portions 414 are threaded loosely through each aperture 410 and 412 to allow one or two-way movement. Frictional adjusting elements 416, which may be adjustable in at least one direction and can preferably be adjustable in one direction and not the other, are located at a segment of extension portion 414 to allow frictional adjusting elements 416 to be moved along a segment of extension portion 414, closer to support portion piece 408, to allow a length between frictional adjusting element 416 and fastener 418 to be reduced (using a one-way frictional adjusting element 416) or reduced and lengthened (using a two-way frictional adjusting element 416).

In use, support portion piece 408 can be placed and adjusted into a desired position to support tissue, and fasteners 418 can be placed at their desired location in the patient. To maintain the desired position of support portion piece 408, frictional adjusting elements 416 can be moved or slid along extension portion piece 414, which may be performed with the help of a cutting and adjustment tool of the invention and as described herein. Movement of extension portion piece 414 can adjust and fix the length of extension portion piece 414 between aperture 412 and tip 418, to adjust and maintain an anatomical position of support portion piece 408. The extension portion piece 414 may then be cut using the adjustment and cutting tool.

Although FIGS. 6A, 6B, and 7 illustrate implants including two extensions, the adjustment and cutting tools of the invention are contemplated to be used with implants that include more or less than two extensions, along with implants that include various shapes and sizes of tissue support portions.

Figure 8:
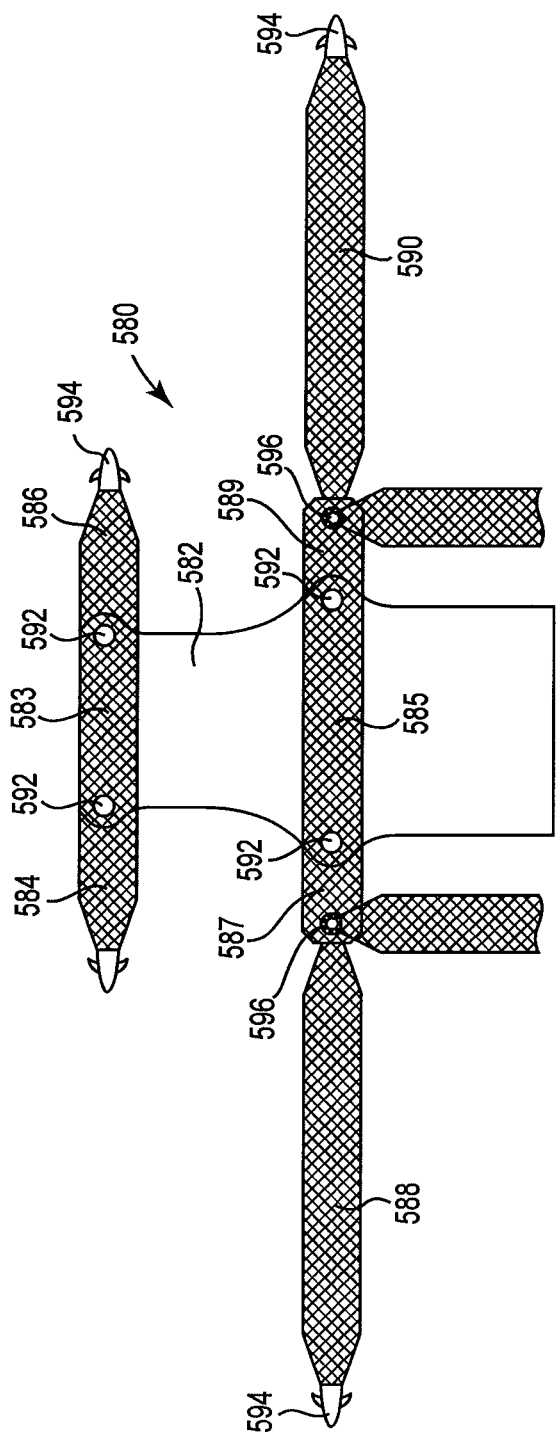
FIG. 8 is a top view of a multi-piece implant and adjustment and cutting tool according to the invention.
Figure 9:
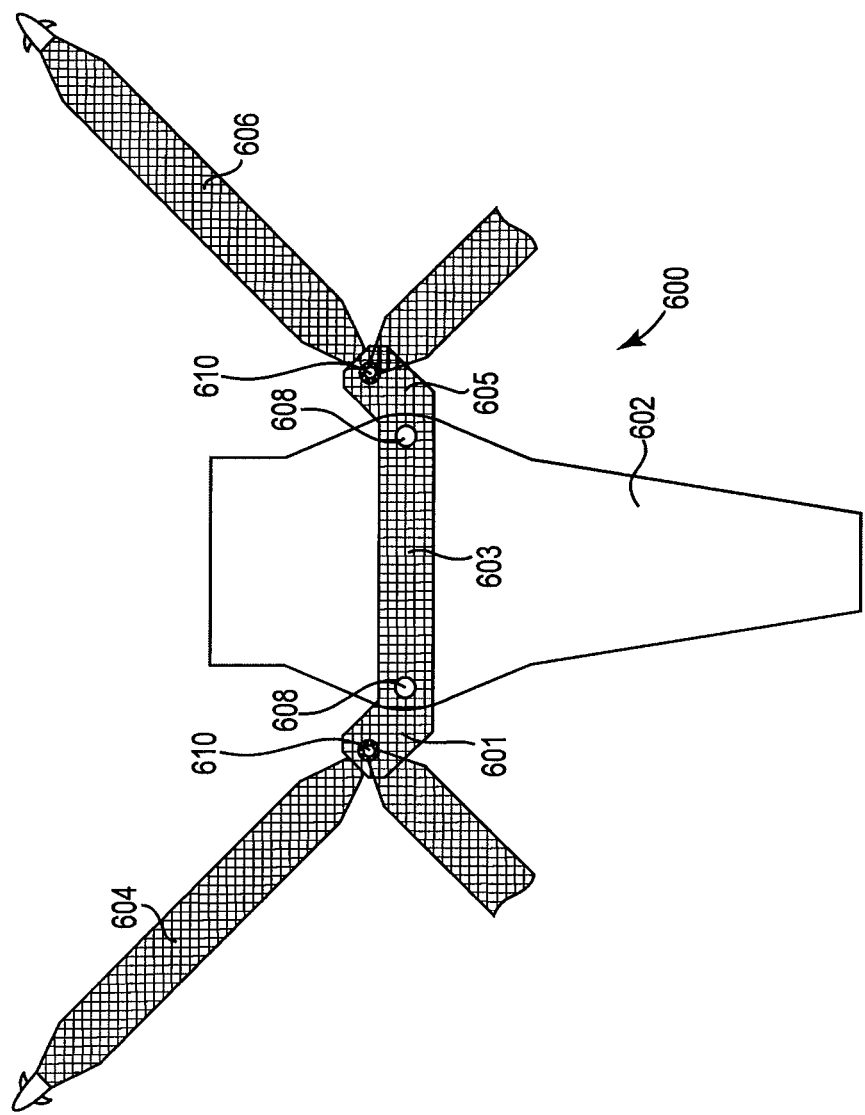
FIG. 9 is a top view of a multi-piece implant and adjustment and cutting tool according to the invention.

FIGS. 8 and 9 illustrate additional embodiments of pelvic implants that include a "multi-layer" or "hybrid" tissue support portion (or support portion piece) made of two layers, one layer being a synthetic layer and a second being biologic layer. Optionally, the hybrid tissue support portion may be incorporated into any implant as described herein, such as into a support portion section of a multi-piece implant that also includes extension portions and a frictional adjusting element as described. Such implants can also be adjusted and cut using the adjustment and cutting tools of the invention.

In particular, FIG. 8 illustrates an exemplary hybrid or multi-layer implant 580, which can be used, for example, for treating anterior vaginal prolapse such as cystocele, optionally in combination with symptoms of urinary incontinence. Implant 580 includes a support portion piece 582, which includes a tissue support portion 586 (e.g., biologic material or mesh), and first and second mesh bands 583 and 585 attached to support portion piece 582 with rivets 592. Superior or "anterior" mesh band 583, as attached to support portion piece 582, provides first and second non-adjustable superior mesh extension portions 584 and 586, each, as illustrated, having a tissue fastener (e.g., self-fixating tip)

594 at a distal end thereof. Superior extension portions 584 and 586 may be designed to support the anterior portion of implant 580, which can support one or more of vaginal tissue, the bladder neck, or urethra, to treat vaginal prolapse and optionally to relieve symptoms of incontinence. Each tissue fastener 594 can be implanted at tissue of the obturator foramen. Alternately, superior extension portions 584 and 586 can be longer and may reach to a retropubic space, an abdominal incision, the pubic bone, or through an obturator foramen and to an external incision at the inner thigh. Superior extension portions 584 and 586 are shown to be of a fixed length, but could alternately be adjustable as described herein. Second mesh band 585, as attached to the support portion piece 582, provides first and second support portion piece arms 587 and 589, each having a frictional adjusting element 596 secured to a distal end. First and second inferior extension portion pieces 588 and 590, having tissue fasteners (e.g., self-fixating tips) 594 at distal ends thereof, are adjustably connected to frictional adjusting element 596, as illustrated, and can be adjusted and cut using the adjustment and cutting tools of the invention.

FIG. 9 illustrates another exemplary pelvic implant, which can be used for treating posterior vaginal prolapse, e.g., apical or vault prolapse, enterocele, rectocele, etc. Implant 600 includes support portion piece 602 made of biologic or mesh material, for example, and substantially making up a tissue support portion, and a reinforcing mesh band 603 extending substantially across the width of support portion piece 602. Reinforcing mesh band 603 is attached to support portion piece 602 with polymeric rivets 608, and provides first and second support portion piece arms 601 and 605. First and second extension portion pieces 604 and 606 connect to support portion piece arms 601 and 605 through frictional adjusting elements 610 at distal ends of support portion piece arms 601 and 605. As with other embodiments of implants described herein, the adjustment and cutting tools of the invention can also be used with the implant embodiment of FIG. 9.

The various systems, apparatus, and methods detailed herein are envisioned for use with known implant and repair systems or improvements thereof (e.g., for male and female), features and methods, including those disclosed in U.S. Pat. Nos. 7,500,945; 7,407,480; 7,351,197; 7,347,812; 7,303,525; 7,025,063; 6,691,711; 6,648,921; and 6,612,977, International Patent Publication Nos. WO 2008/057261, WO 2007/097994, WO 2007/149348, WO 2009/017680, and U.S. Patent Publication Nos. 2002/151762, 2010/0174134, 2010/0298630, 2002/0028980, 2006/0069301, and 2002/147382, and International Application number PCT/US10/62577 (filed Dec. 30, 2010). Accordingly, the above-identified disclosures are fully incorporated herein by reference in their entirety.

An implant for placement by use of the described tools, methods, and anchors (e.g., helical anchors, self-fixating tips, or otherwise), and their various components, structures, features, materials and methods may have a number of suitable configurations as shown and described in the previously-incorporated references or as described herein or elsewhere. Various methods and tools for introducing, deploying, anchoring, and manipulating implants to treat incontinence, prolapse, or another pelvic condition, as disclosed in the previously-incorporated references are envisioned for possible adapted use with devices and methods described herein.

An implant for use as described herein can include any structural features useful for a desired treatment, including any desired size, shape, and optional features such as adjustability. Any of these features may be previously known, or described in documents incorporated herein, or as described herein, for any particular implant and method. An implant that includes or is otherwise secured, adjusted, and manipulated as described might be useful to treat any type of pelvic condition in a male or a female patient; as a single and non-limiting example, implants and methods as described be used in an abdominal, laparascopic and/or transvaginal SCP procedure to provide support to vaginal tissue (e.g. a vaginal cuff), through an implant attached at a region of sacral anatomy such as a sacral ligament (e.g., anterior longitudinal ligament, a.k.a. the "anterior ligament" or "longitudinal ligament").

One type of a tissue fastener that can be used with devices and methods of the invention is a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region (e.g., at a location of an obturator foramen). The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCT US2007/004015, the entirety of which is incorporated herein by reference. Other structures may also be useful.

A self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instruments, insertion tools, adjusting tools, or the like, may be incorporated or used with an implant or method as described. Examples of useful tools include those that generally include one or more (stationary or moveable) thin elongate, relatively rigid shafts or needles that extend from a handle. The shaft can be a single elongate shaft or multiple separate elongate shafts extending from the handle, or one or more primary shafts that extend from the handle and that contain multiple branch or "tine" shafts that separate at the end of the primary shaft. The handle is located at a proximal end of the device and attaches to one end of a shaft. According to some embodiments, a distal end of one or more shafts can be adapted to engage a portion of an implant, such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT Application Nos. 2006/028828 and 2006/0260618; WO 2010/093421; and U.S. Patent Publication No. US 2010/0256442, the entireties of which are all incorporated herein by reference.

Optionally, an implant can include a tissue fastener at a location of a tissue support portion, or at a location along a length of an extension portion. This form of tissue fastener can be in the form of reinforced (e.g., by coating, heat treating, or a reinforcing weave or strip) edge extensions, multiple layers of mesh and edge extensions in an extension portion, etc., as described, for example, at Applicant's copending U.S. Pat. No. 7,422,557, and Applicant's copending United States Patent Publication Numbers US 2006/0195011, US 2006/0195007, and US 2006/0195010, all of which are incorporated herein by reference. Other examples include relatively rigid structures such as metal, plastic, or other polymeric or non-polymeric structure that may be shaped to frictionally engage soft tissue, for example to include a tine, hook, chevron, barb, arrow, etc., combinations thereof, or any structure added to an edge or surface of an extension portion to improve fixation within tissue. The structure can have any shape or form that will increase frictional force between the implant and adjacent tissue, such as one or multiple pointed surface directed along a length of an extension portion, toward the tissue support portion, and extending away from a surface or edge of the implant (e.g., extension portion). The tissue fastener can be located at a position of an implant that will result in the tissue fastener being located at supportive tissue such as muscle or fascia when the implant is placed with a midline of the tissue support portion being located below a urethra. For example, a tissue fastener may be located on a tissue support portion or an extension portion of an implant, e.g., as close as 2 or 3 centimeters from a midline of a tissue support portion, and up to a distance that reaches tissue of an obturator foramen when the midline is located below a urethra, e.g., up to 7 centimeter from the midline.

According to embodiments of implants described below, an implant can include multiple pieces that are adjustably connected together by an adjusting engagement. An extension portion piece can be separate from a support portion piece, and the two pieces can be connected through an adjustable engagement, wherein the support portion piece can include a tissue support portion.

Figure 10:
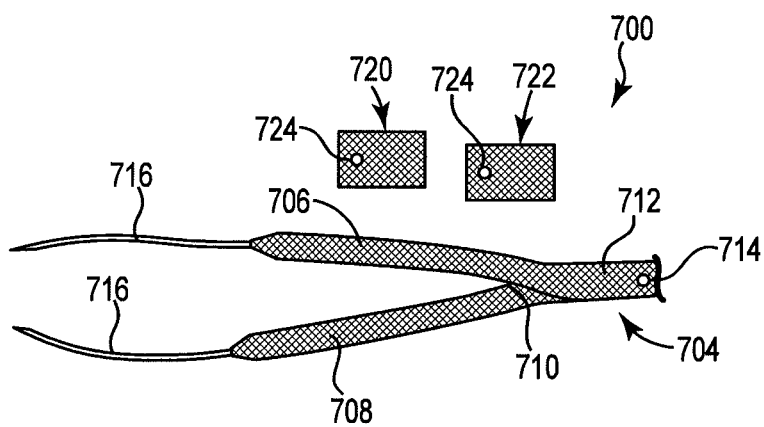
FIG. 10 is a top view of an embodiment of an adjustable implant of the invention.

Referring now to FIG. 10, an embodiment of an implantable system 700 is illustrated, which can be used for vaginal vault suspension and attachment to the sacral promontory. This implantable system 700 advantageously allows for independent tensioning of the anterior and posterior vaginal compartments. In particular, the implantable system of this embodiment includes a Y-shaped mesh component 702 that is designed to be attached to the sacral promontory at a first end that is generally designated by reference number 704. The Y-shaped mesh component 704 includes two elongated mesh portions 706, 708 that are arranged in a V-shape to provide an intersection or apex area 710. Alternatively, one or more of these elongated mesh portions 706, 708 can instead be an elongated polymeric portion. An extending base portion 712 extends from the apex area 710 where the two elongated mesh portions 706, 708 meet. As illustrated, the extending base portion 712 includes at least one eyelet or opening 714, which can be used for attachment of this portion to the sacral promontory, for example. A rod 716 can extend from one or both of the elongated mesh portions 706, 708, as illustrated, which can have a variety of different lengths and cross-sections, as desired. The elongated mesh portions 706, 708 are illustrated as being generally flat rectangular members that taper at one end, however, it is understood that the elongated mesh portions 706, 708 can instead have a different configuration.

This system further includes two apical mesh pieces, which may be referred to as an anterior apical mesh piece 720 and a posterior apical mesh piece 722. The anterior and posterior apical mesh pieces 720, 722 can be sutured or otherwise attachable to anterior and posterior vaginal walls, respectively. These mesh pieces 720, 722 can each be provided with an eyelet or opening 724 that is configured to accept an end of one of the rods 716 that extend from an elongated mesh portions 706, 708, as described above. In one embodiment, one or both of the eyelets 724 is a one-way locking eyelet such that when a rod 716 is pushed through the eyelet 724 in an insertion direction, it is prevented from being pulled back out of the eyelet (i.e., in a direction that is opposite from the insertion direction). In any case, the attachment between the rod 716 and the eyelet 724 provides adjustability to the connection, in that a length of the rod 716 can be pushed through the eyelet 724 until a specific tension on the device is achieved. In a similar manner, the eyelet 724 of the extending base portion 712 is provided for adjustable attachment of the device to the sacral promontory. That is, the eyelet 724 of the extending base portion 712 is moveable relative to the sacral promontory to provide additional adjustability to the system.

A tool such as a tensioning device (not shown) and/or an adjustment and cutting tool can optionally be used to push the eyelet further along the length of the elongated mesh portion and/or the base portion until a specific tension has been reached. A tool that includes a tension indicator gauge to measure tension can also be used, if desired. In addition, a tool can be provided to move the rectum out of the way to provide a clear view of the sacrum during the surgical procedure.

The system of FIG. 1 provides for an adjustability mechanism that is designed to allow for elevation of the vaginal apex toward the sacrum in order to alleviate the symptoms of vaginal prolapse. In one embodiment of the invention, the system can include a Y-shaped mesh component that is made up of the anterior and posterior vaginal mesh pieces and a sacral attachment piece equipped with one rod (e.g., a plastic rod) that can be inserted through a locking eyelet that is provided on the Y-shaped mesh component. Such a configuration can provide elevation of the vaginal apex. This system therefore is provided with adjustability at both the vaginal walls and at the sacrum or sacral promontory, and can be used with either transvaginal, abdominal, and/or laproscopic methods of supporting the apex of a vagina by fixation and support from a region of the sacral anatomy.

Figure 11:
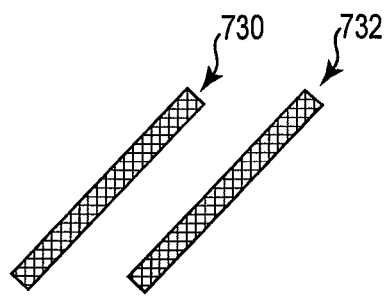
FIG. 11 is a top view of anterior and posterior mesh pieces useful with embodiments of the invention.
Figure 12:
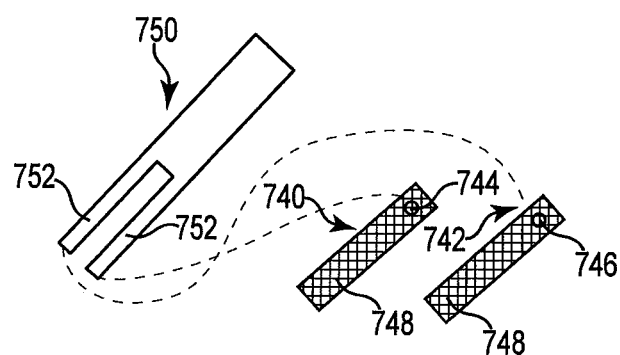
FIG. 12 is a top view of the mesh pieces of FIG. 11, along with a Y-shaped implant member, in accordance with the invention.

Referring now to FIGS. 11-15, adjustable vaginal apex support systems are illustrated, which provide for separate tensioning to the anterior and posterior compartments. With reference first to FIG. 11, a sacral colpopexy or related procedure for supporting a vaginal apex can be performed using an anterior implant 730 and a posterior implant 732. The anterior implant 730 is attachable to a region of sacral anatomy (e.g., an anterior longitudinal ligament) at a posterior end, and to a vaginal wall (e.g., an anterior vaginal wall) at an anterior end. The posterior implant 732 is attachable to a region of sacral anatomy at a posterior end, and to a vaginal wall (e.g., a posterior vaginal wall) at an anterior end. These separate mesh pieces allow for independent adjustment in vivo to obtain desired support for a vaginal apex With additional reference to FIG. 12, an anterior implant 740 and a posterior implant 742 are illustrated, each of which includes an aperture or eyelet 744, 746, respectively, located adjacent to one of its ends. Each of these implants 740, 742 can include an extending portion 748 that extends beyond the area of the aperture or eyelet 744, 746, wherein this extending portion allows for extra anterior or posterior support. This vaginal apex support system further includes an additional member 750 that is provided for fixation to the sacrum. That is, FIG. 12 shows an adjustable implant system including an adjustable vaginal apex support device that includes an anterior piece 740, a posterior piece 742, and an auxiliary piece 750 that is designed for fixation to the sacrum. These pieces are used in a system that allows for separate adjustment in vivo to obtain proper support of a vaginal apex. The anterior and posterior pieces 740, 742 are securable to an anterior and a posterior vaginal wall, respectively. The auxiliary piece 750 is securable to a region of sacral anatomy (e.g., an anterior longitudinal ligament or the sacrum). Extension pieces 752 of the auxiliary implant 750 are inserted through eyelets 744, 746 on the anterior and posterior pieces. Each extension piece 752 can be adjusted through its corresponding eyelet, and tensioned separately at the vaginal apex with the auxiliary piece being secured to the sacral anatomy. By selective movement of the extension pieces through the eyelets or openings (e.g., grommets or alternate frictional or locking apertures), tension of the combined mesh implant and positioning and support of the vaginal apex can be adjusted.

Figure 13:
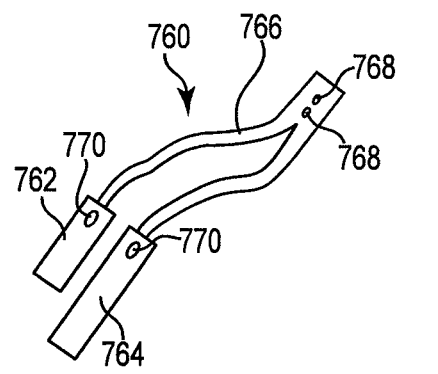
FIG. 13 is a top view of an embodiment of an implant of the invention.
Figure 14:
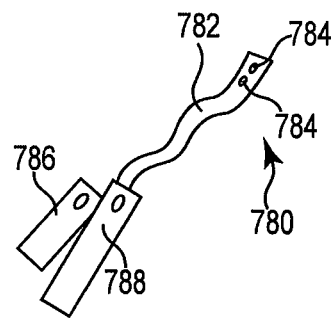
FIG. 14 is a top view of an embodiment of an implant of the invention.

FIGS. 13 and 14 illustrate two additional embodiments of implant systems of the invention, wherein a system 760 of FIG. 13 includes an anterior vaginal mesh 762 attached to one extending arm or portion of a sacral mesh 766 and a posterior vaginal mesh 764 attached to a separate extending arm or portion of the sacral mesh 766. The sacral mesh 766 is provided with a base portion having one or more apertures 768 (e.g., two apertures), from which the two arms extend. The distal ends of these arms are attached to apertures or openings 770 of the anterior and posterior mesh portions 762, 764. Another embodiment of an implant system 780 is illustrated in FIG. 14, which includes a sacral mesh 782 having one or more apertures 784 (e.g., two apertures) adjacent to a first end, but that does not branch into two arms. Instead, the sacral mesh 782 of this embodiment is a single strip of mesh material that includes an attachment member extending from a second end (which is at the opposite end from the first end) that attaches to both an anterior mesh 786 and a posterior mesh 788. For example, the attachment member can be a rod or post that extends through an aperture of both the anterior mesh 786 and the posterior mesh 788. With both of these embodiments, the length and positioning of the implant can be adjusted at the apertures of any or all of the anterior mesh, the posterior mesh, and the sacral mesh.

Figure 15:
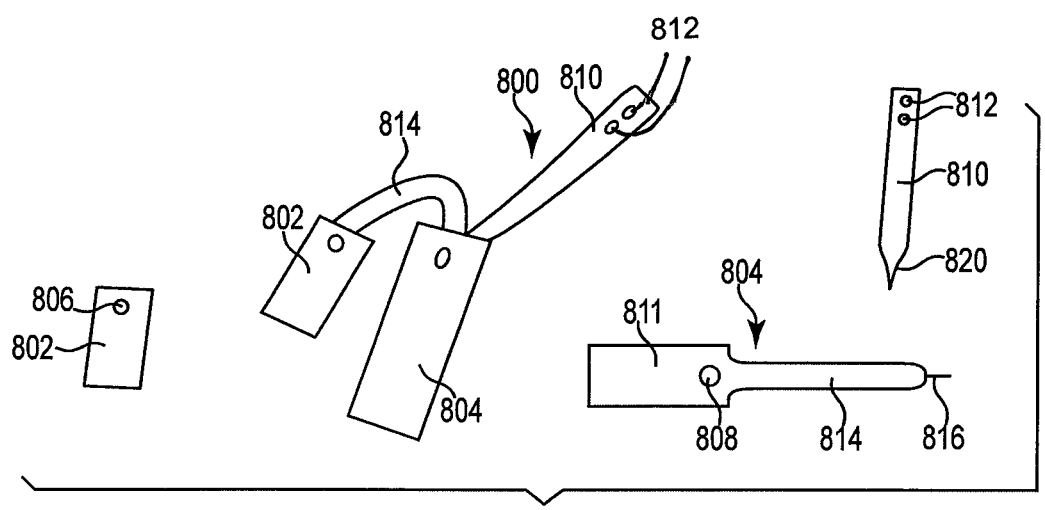
FIG. 15 is a top view of an embodiment of an implant system with some of the system components shown both assembled and separately, in accordance with the invention.

FIG. 15 illustrates another embodiment an implant system 800 of the invention, with components illustrated both assembled and separately. System 800 allows anterior and posterior portions to tension independently, which only requires one arm at a time. In particular, this system 800 includes an anterior mesh portion 802 and a posterior mesh portion 804, each of which includes at least one hole or aperture 806, 808, respectively. In this Figure, the posterior mesh portion 804 is illustrated as having a configuration that includes a base member 811, an arm member 814 extending from the base member 811, and a rod 816 extending from the arm member 814. The auxiliary piece 810 of this system, which is attachable to the sacrum, for example, is a single elongated piece, rather than being Y-shaped with extending arms, as in some other embodiments described herein. The auxiliary piece 810 includes at least one aperture 812 adjacent to one end, and a rod 820 extending from its other end.

In order to assemble the components of this system 800, the arm member of the posterior mesh portion 804 is positioned relative to the anterior mesh portion 802 so that its rod 816 can engage with or extend through an aperture 806 of the anterior mesh portion 802. The rod 820 extending from the auxiliary portion 810 is positioned relative to the posterior mesh portion 804 so that it can engage with or extend through an aperture 808 of the posterior mesh portion 804. In this way, the posterior mesh portion 804 can be adjusted first, and then the anterior mesh portion 802 can be subsequently adjusted via the arm member of the posterior mesh portion 804. This embodiment is further advantageous in that the single arm tensioning provided by the auxiliary portion 810 can prevent and/or minimize twisting of the mesh during and after surgical procedures, and can also prevent and/or minimize any confusion regarding the proper orientation and arrangement of the components relative to each other. Although the description of this embodiment indicates that the posterior mesh portion includes a base member, an arm member, and a rod, while the anterior mesh portion basically includes only a base member, it is understood that these pieces may instead be configured such that the anterior mesh portion is the component that includes a base member, an arm member, and a rod, while the posterior mesh portion then includes only a base member. The components can be assembled in the same manner as discussed above.

The disclosed systems, their various components, structures, features, materials and methods may have a number of suitable configurations as shown and described in the previously-incorporated references. Various methods and tools for introducing, deploying, anchoring and manipulating devices, implants, and the like as disclosed in the references incorporated herein are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A medical device comprising:
a multi-piece implant including an elongate portion piece, a support portion piece, and an adjustable element, the elongate portion piece adjustably extending from the support portion piece at the adjustable element, the elongate portion piece including a mesh portion; and
an adjusting and cutting tool including a distal end portion engageable with the elongate portion piece to facilitate adjusting of the elongate portion piece relative to the support portion piece and to facilitate cutting of the elongate portion piece, the distal end portion including an opening extending through a thickness of the distal end portion, the elongate portion piece configured to be inserted through the opening, the distal end portion including a cutting member extending into an interior of the opening, the cutting member includes at least two cutting surfaces that are angled relative to each other within the opening.

2. The medical device according to claim 1, wherein movement of the tool in a first direction facilitates adjusting of the elongate portion piece relative to the support portion piece and wherein movement of the tool in a second direction, which is different from the first direction, facilitates cutting of the elongate portion piece.

3. The medical device according to claim 1, wherein the tool comprises an elongate shaft, a proximal end portion, and the distal end portion, wherein the distal end portion is engageable with the elongate portion piece.

4. The medical device according to claim 1, wherein the tool comprises a longitudinal axis and wherein the cutting member is positioned at an angle relative to the longitudinal axis.

5. The medical device according to claim 1, wherein the elongate portion piece comprises an anchor at a distal end of the elongate portion piece, the anchor comprising one of a helical anchor and a self-fixating tip.

6. The medical device according to claim 1, wherein the opening is a through-aperture such that the elongate portion piece is configured to pass through the distal end portion via the through-aperture.

7. The medical device according to claim 1, wherein the cutting member is oriented to produce a cut in the elongate portion piece located at the interior of the opening, by pulling the tool in a proximal direction.

8. The medical device according to claim 1, wherein the cutting member is oriented to produce a cut in a direction that is non-perpendicular and non-parallel to a longitudinal axis of the opening.

9. The medical device according to claim 1, wherein the two cutting surfaces intersect to form a V-shape within the opening.

10. The medical device according to claim 1, wherein movement of the tool in a direction away from a user facilitates manipulation of the elongate portion piece relative to the support portion piece without cutting the elongate portion piece and wherein movement of the tool in a direction toward the user facilitates cutting of the elongate portion piece.

11. The medical device according to claim 1, wherein the adjustable element comprises an aperture through which the elongate portion piece is threaded.

12. The medical device according to claim 1, wherein the adjusting and cutting tool is configured to move along the elongate portion piece in an adjustment direction until the distal end portion of the tool contacts the adjustable element.

13. An adjusting and cutting tool comprising:
an elongate shaft;
a distal end portion extending from the elongate shaft, the distal end portion having a first surface and a second surface opposite to the first surface, the distal end portion including a first opening on the first surface of the distal end portion, a second opening on the second surface of the distal end portion, and a channel extending between the first opening and the second opening, the distal end portion including a cutting member having at least two cutting surfaces that are angled relative to each other within the channel, the channel being engageable with a mesh portion of an implantable article to facilitate manipulation of the mesh portion relative to a support portion of the implantable article and to facilitate cutting of the mesh portion via the cutting member; and
a proximal end portion extending from the elongate shaft.

14. The adjusting and cutting tool of claim 13, wherein the cutting member is fixed and non-moveable relative to the channel.

* * * * *